United States Patent [19]

Maruta et al.

[11] Patent Number: 5,089,628

[45] Date of Patent: Feb. 18, 1992

[54] FLUORINE-CONTAINING BISMALEAMIC ACIDS AND BISMALEIMIDES USEFUL FOR THERMOSETTING RESINS

[75] Inventors: Masamichi Maruta, Kawagoe; Akihiro Fukui, Kamifukuoka, both of Japan

[73] Assignee: Central Glass Company, Limited, Ube, Japan

[21] Appl. No.: 410,494

[22] Filed: Sep. 21, 1989

[30] Foreign Application Priority Data

Sep. 22, 1988 [JP]  Japan .................................. 63-237898
Dec. 21, 1988 [JP]  Japan .................................. 63-322538

[51] Int. Cl.$^5$ .......................................... C87D 207/452
[52] U.S. Cl. ................................. 548/521; 548/452; 548/520
[58] Field of Search ............... 548/520, 521, 522, 452

[56] References Cited

U.S. PATENT DOCUMENTS 4,866,185  9/1989  Hartmann et al. .................... 548/522
4,904,801  2/1990  Butter et al. ......................... 548/521

FOREIGN PATENT DOCUMENTS 2589869  11/1985  France .................................. 548/521
1117861  10/1987  Japan .................................... 548/549
8703871  7/1987  World Int. Prop. O. .......... 548/521

*Primary Examiner*—C. Warren Ivy
*Assistant Examiner*—Celia Chang
*Attorney, Agent, or Firm*—Fleit, Jacobson, Cohn, Price, Holman & Stern

[57] ABSTRACT

The invention provides novel fluorine-containing bismaleimides represented by the general formula shown below. The bismaleimides are obtained by dehydrating and cyclizing reaction of corresponding bismaleamic acids which are also novel compounds. For example, maleic anhydride is used for preparing the bismaleamic acids. A mixture of a bismaleimide of the invention and a diamine is useful as a thermosetting resin composition. At 100°-300° C. the resin composition undergoes addition polymerization to turn into a solid resin which are high in moisture resistance and low in dielectric constant. For use in the resin composition it is preferable that both $R^1$ and $R^2$ in the general formula of the bismaleimide are $-CF_3$.

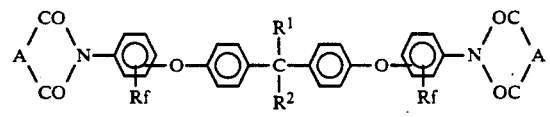

wherein A represents a divalent organic group having an ethylenic unsaturated bond; Rf represents fluorine atom or a perfluoroalkyl group; $R^1$ and $R^2$ are the same or different and each represent hydrogen atom, methyl group, ethyl group or a halogenated methyl group; and each $-N<$ is at the m- or p-position with respect to the aromatic ether bond $-O-$.

6 Claims, 2 Drawing Sheets

FLUORINE-CONTAINING BISMALEAMIC ACIDS AND BISMALEIMIDES USEFUL FOR THERMOSETTING RESINS

BACKGROUND OF THE INVENTION

This invention relates to a group of novel fluorine-containing aromatic bismaleamic acids (bismaleinamic acids), aromatic bismaleimides (bismaleinimides) derived from the bismaleamic acids and thermosetting resin compositions of addition polymerization type using the bismaleimides. The resin compositions provide solid imide resins excellent in heat resistance and moisture resistance and low in dielectric constant and will have wide uses in electric and electronic devices, optical devices, machine parts, etc.

Polyimide resins obtained by addition polymerization of a bismaleimide are generally excellent in heat resistance and have good electrical and mechanical characteristics. Accordingly polyimide resins of this type have been used as industrial materials in electronic devices and various machines.

However, conventional polyimide resins of the addition polymerization type are relatively high in moisture absorption and moisture permeability and, by absorption of moisture, suffer from lowering of dimensional stability and/or adhesive power. Therefore, when the resins are used, for example, as sealants in integrated circuits or as substrates of printed circuits there are doubts about longterm reliability of the devices. From another aspect, it is not seldom that thermosetting resins for use in electronic devices are required to be low in dielectric constant, but most of conventional imide resins of the addition polymerization type do not meet this requirement.

SUMMARY OF THE INVENTION

It is an object of the present invention to provide a novel imide resin of addition polymerization type, which is high in moisture resistance and low in dielectric constant.

It is another object of the invention to provide a novel bismaleimide which serves as the principal material of the aforementioned novel imide resin.

It is still another object of the invention to provide a novel bismaleamic acid from which the novel bismaleimide is derived.

The present invention provides a bismaleamic acid represented by the general formula (1):

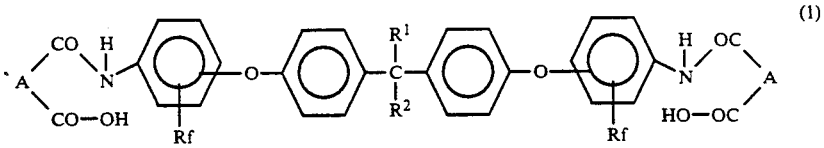

wherein A represents a divalent organic group having an ethylenic unsaturated bond; Rf represents fluorine atom or a perfluoroalkyl group; $R^1$ and $R^2$ are the same or different and each represent hydrogen atom, methyl group, ethyl group or a halogenated methyl group; and each —NH— is at the m- or p-position with respect to the aromatic ether bond —O—.

Furthermore, the invention provides a bismaleimide represented by the general formula (2):

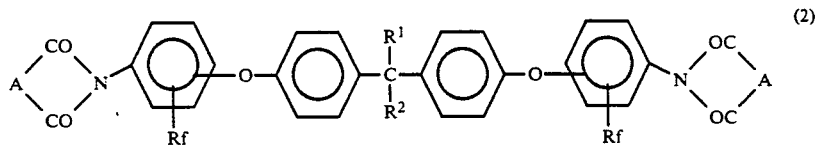

wherein A, Rf, $R^1$ and $R^2$ are as defined above with respect to the general formula (1), and each —N< is at the m- or p-position with respect to the aromatic ether bond —O—.

A bismaleamic acid represented by the general formula (1) is prepared usually by reacting an aromatic diamine represented by the general formula (3) with an unsaturated dicarboxylic acid anhydride represented by the general formula (4) in an organic solvent, though this method is not limitative.

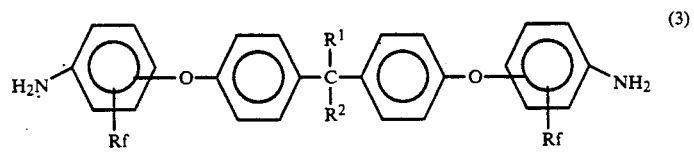

wherein Rf, $R^1$ and $R^2$ are as defined above with respect to the general formula (1), and each —NH$_2$ is at the m- or p-position with respect to —O—.

wherein A is as defined above with respect to the general formula (1).

For this reaction it is preferable to select an aromatic diamine in which Rf and/or $R^1$ and $R^2$ in the general formula (3) are perfluoroalkyl groups.

A bismaleimide represented by the general formula (2) is obtained by subjecting a corresponding bismaleamic acid represented by the general formula (1) to a dehydrating and cyclizing reaction.

Further, the invention provides a thermosetting resin composition comprising a bismaleimide represented by the general formula (1) and a diamine represented by the general formula (5):

$$H_2N-Y-NH_2 \qquad (5)$$

wherein Y represents a divalent organic group.

For this resin composition it is preferred to use a bismaleimide in which both $R^1$ and $R^2$ in the general formula (2) are $-CF_3$ groups, i.e. a bismaleimide represented by the general formula (2A):

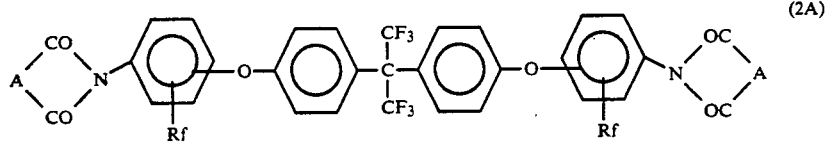

wherein A and Rf, and the position of each $-N<$ are as defined hereinbefore with respect to the general formula (2).

Such a bismaleimide is obtained by reaction of a diamine represented by the general formula (3A) with an unsaturated dicarboxylic acid anhydride represented by the general formula (4).

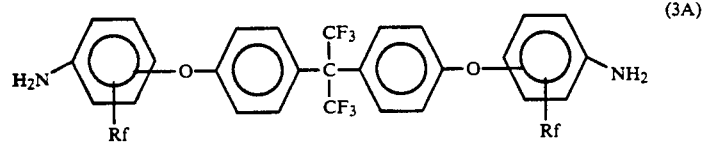

wherein Rf and the position of each $-NH_2$ are as defined hereinbefore with respect to the general formula (3).

A thermosetting resin composition according to the invention can easily be cured into a solid imide resin by heating the resin composition to carry out addition polymerization of the bismaleimide with the diamine.

A bismaleimide of the invention is either an amorphous material or a crystalline materaial relatively low in melting point. When this bismaleimide is suitably selectively combined with a noncrystalline or low melting point diamine (represented by the general formula (5) ), such as a noncrystalline diamine represented by the general formula (3), the resultant mixture becomes wax-like or fluidic at a relatively low temperature in the range of from about 50° C. to about 100° C. This is very convenient for shaping of the mixture, viz. a resin composition according to the invention.

The thermosetting resin compositions according to the invention provide heat resistant imide resins which are excellent in moisture resistance and very low in dielectric constant and possess good mechanical characteristics. Accordingly these imide resins will have wide uses in electric and electronic devices, optical devices and various machine parts.

DESCRIPTION OF THE PREFERRED EMBODIMENTS

Figure 1:
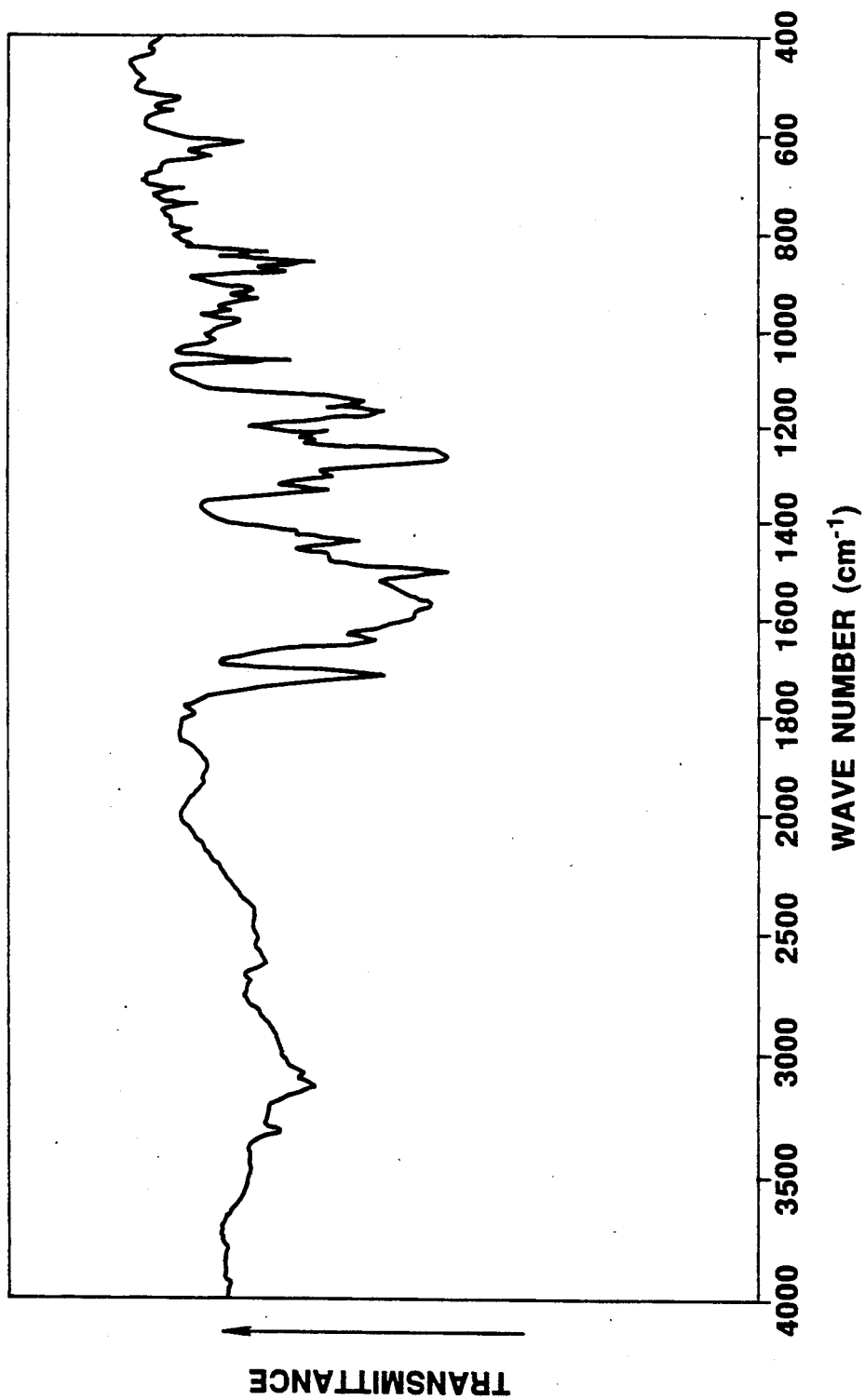
FIG. 1 shows the infrared absorption spectrum pattern of a bismaleamic acid prepared as an example of the present invention.

In preparing a bismaleamic acid represented by the general formula (1) by the reaction of an aromatic diamine represented by the general formula (3) with an unsaturated dicarboxylic acid anhydride represented by the general formula (4), an organic solvent is used as a liquid medium for the reaction. For example, the solvent can be selected from N,N-dimethylformamide, N,N-dimethylacetamide, N-methyl-2-pyrrolidone, N-methylcaprolactam, dimethylsulfoxide, tetrahydrofuran, dioxane, acetone, ethylemethyl ketone and ethyl acetate.

The following compounds are named as suitable examples of fluorine-containing aromatic diamines represented by the general formula (3): 2,2-bis[4-(4-amino-2-trifluoroemthylphenoxy)phenyl]hexafluoropropane, 2,2-bis[4-(4-amino-2-fluorophenoxy)phenyl]hexafluoropropane, 2,2-bis[4-(4-amino-2-nonafluorobutylphenoxy)phenyl]hexafluoropropane, 2,2-bis[4-(4-amino-2-tridecafluorohexylphenoxy)phenyl]hexafluoropropane, 2,2-bis[4-(4-amino-2-heptadecafluorooctylphenoxy)phenyl]hexafluoropropane, 2,2-bis[4-(4-amino-3-trifluoromethylphenoxy)phenyl]hexafluoropropane, 2,2-bis[4-(4-amino-3-fluorophenoxy)-phenyl]hexafluoropropane, 2,2-bis[4-(4-amino-3-nonafluorobutylphenoxy)phenyl]hexafluoropropane, 2,2-bis[4-(4-amino-3-tridecafluorohexylphenoxy)phenyl]hexafluoropropane, 2,2-bis[4-(4-amino-3-heptadecafluorooctylphenoxy)phenyl]hexafluoropropane, 2,2-bis[4-(3-amino-5-trifluoromethylphenoxy)phenyl]hexafluoropropane, 2,2-bis[4-(3-amino-5-fluorophenoxy)phenyl]hexafluoropropane, 2,2-bis[4-(3-amino-5-nonafluorobutylphenoxy)phenyl]hexafluoropropane, 2,2-bis[4-(3-amino-5-tridecafluorohexylphenoxy)phenyl]hexafluoropropane, 2,2-bis[4-(3-amino-5-heptadecafluorooctylphenoxy)phenyl]hexafluoropropane, 2,2-bis[4-(4-amino-2-trifluoromethylphenoxy)phenyl]-propane, 2,2-bis[4-(4-amino-3-trifluoromethylphenoxy)-phenyl]propane and 2,2-bis[4-(3-amino-5-trifluoromethylphenoxy)phenyl]propane.

Good examples of unsaturated dicarboxylic acid anhydrides represented by the general formula (4) are maleic anhydride, chloromaleic anhydride, dichloromaleic anhydride, citraconic anhydride, mesaconic anhydride, and tetrahydrophthalic anhydride.

In most cases the reaction between one of the above diamines and one of the above acid anhydrides proceeds at room temperature.

A bismaleimide represented by the general formula (2) is obtained by subjecting a bismaleamic acid represented by the general formula (1) to a dehydrating and cyclizing reaction. For this reaction it is suitable to use 2.10-3.0 mols of acetic anhydride per mol of the bismaleamic acid with addition of 0.6-2.0 mols of triethylamine, sodium acetate, potassium acetate, sodium carbonate or potassium carbonate. Optionally a catalyst such as cobalt or nickel may be used. Also it is optional to carry out the dehydrating and cyclizing reaction in an organic solvent which is azeotropic with water in the presence of an acid catalyst.

A bismaleimide of the invention undergoes addition polymerization reaction with a diamine represented by the general formula (5) at elevated temperatures to give a solid resin. Therefore, a mixture of the bismaleimide and the diamine is useful as a thermosetting resin composition. It is preferable that the bismaleimide is one represented by the general formula (2A). Examples of useful diamines are m-phenylenediamine, p-phenylenediamine, 3,3'-dimethyl-4,4'-diaminobiphenyl, 3,3'-dichlorobenzidine, 3,3-dimethoxybenzidine, 4,4'-diaminodiphenylmethane, 1,1-bis(4-aminophenyl)ethane, 2,2-bis(4-aminophenyl)propane, 2,2-bis(4-aminophenyl)hexafluoropropane, 2,2-bis(4-aminophenyl)-1,3-dichloro-1,1,3,3-tetrafluoro-propane, 4,4'-diaminodiphenyl ether, 4,4'-diamino-diphenyl sulfide, 3,3'-diaminodiphenyl sulfide, 4,4'-diaminodiphenyl sulfoxide, 4,4'-diaminodiphenylsulfone, 3,3'-diaminodiphenylsulfone, 3,3'-diaminobenzophenone, 4,4'-diaminobenzophenone, 3,4'-diaminobezophenone, N,N-bis(4-aminophenyl)aniline, N,N-bis(4-aminophenyl)methylamine, N,N-bis(4-aminophenyl)-n-butylamine, N,N-bis(4-aminophenyl)amine, m-aminobenzoyl-p-aminoanilide, 4-aminophenyl-3-aminobenzoate, 4,4'-diaminoazobenzene, 3,3'-diaminoazobenzene, bis(4-aminophenyl)-diethylsilane, bis(4-aminophenyl)phenylphosphine oxide, bis(4-aminophenyl)ethylphsophine oxide, 1,5-diaminonaphthalene, 2,6-diaminopyridine, 2,5-diamino-1,3,4-oxadiazole, m-xylylenediamine, p-xylylenediamine, 2,4-(p-$\beta$-amino-tertbutylphenyl)ether, p-bis-2-(2-methyly-4-aminopentyl)benzene, p-bis(1,1-dimethyl-5-aminopentyl)benzene, hexamethylenediamine, nonamethylenediamine, decamethylenediamine, 2,11-diaminododecane, 1,12-diaminooctadecane, 2,2-dimethylpropylenediamine, 3-methylheptamethylenediamine, 2,5-dimethylheptamethylenediamine, 4,4-dimethylheptamethylenediamine, 5-methylnonamethylenediamine, 1,4-diaminocyclohexane, bis(p-aminocyclohexyl)-methane, 3-methoxyhexamethylenediamine, 1,2-bis(3-aminopropoxy)ethane, bis(3-aminopropyl)sulfide, N,N-bis(3-aminopropyl)methylamine, 2,5-diaminobenzotrifluoride, 2,5-diaminononafluorobutylbenzene, 4,4'-diamino-2,2'-bistrifluoromethylbiphenyl, 2,2bis[4-(4-aminphenoxy)-phenyl]hexafluoropropane, 2,2-bis(3-amino-4-hydroxy-phenyl)hexafluoropropane, 2,2-bis(3-amino-4-methyl-phenyl)hexafluoropropane, and diamines represented by the general formula (3). If desired at least two of these diamines can be used jointly.

In the thermosetting resin composition it is preferred that the molar ratio of the bismaleimide to the aromatic diamine(s) falls in the range from 10:1 to 1:1.

The curing of a resin composition according to the invention is accomplished by heating at 100°-300° C. for several minutes to about 15 hours. The manner of heating is not strictly limited. That is, the curing may be made either by simply heating the resin composition up to a predetermined curing temperature or by first partially curing the resin composition into a prepolymer by mild heating and then heating the prepolymer to a degree sufficient for full curing. In the latter case, it is also possible to prepare the prepolymer by heating a solution of the resin composition in an organic solvent in the presence of an acid catalyst and pouring the heat-treated solution into a poor solvent thereby precipitating the prepolymer.

Optionally, a polymerization initiator is added to a resin composition according to the invention for the purpose of completing the heat curing in a relatively short time. It is suitable to select the initiator from organic peroxides such as benzoyl peroxide, p-chlorobenzoyl peroxide, 2,4-dichlorobenzoyl peroxide, caprylyl peroxide, lauroyl peroxide, acetyl peroxide, methylethyl ketone peroxide, cyclohexanol peroxide, bis(1-hydroxy-cyclohexyl peroxide), hydroxyheptyl peroxide, tert-butyl hydroperoxide, p-menthane hydroperoxide, tert-butyl perbenzoate, tert-butyl peracetate, tert-butyl peroctoate, tert-butyl peroxyisobutyrate and di-tert-butyl diperphthalate. If desired two or more of these peroxides may be used jointly. Besides the initiator, it is optional to add an accelerator which can be selected from, for example, mercaptans, sulfites, $\beta$-diketones, metal chelates and metallic soaps.

According to the need, a resin composition according to the invention may contain any of the following additives.

For improving storage stability of the resin composition at normal temperature, a polymerization inhibitor can by selected from, for example, quinones such as p-benzoquinone, naphthoquinone and phenanthraquinone, phenols such as hydroquinone, p-tert-butylcatecol and 2,5-di-tert-butylhydroquinone, nitro compounds and metal salts.

When the resin composition is to be used for molding purposes, the composition may contain an inorganic filler such as zirconia, silica, alumina, aluminum hydroxide, titania, zinc oxide, calcium carbonate, magnesite, clay, kaolin, talc, mica, silica sand, glass, quartz glass, asbestos, metal or ceramic whiskers, carbon black, graphite or molybdenum disulfide, and/or a coupling agent such as epoxysilane, vinylsilane, borane or alkoxytitanate.

Another example of the optional additives is a flame retartant which can be selected from halogen compounds, phosphor compounds and antimony oxide.

EXAMPLE 1

In a 100-ml four-necked flask provided with thermometer, stirrer and cooling pipe, 5.0 g (7.6 mmol) of 2,2-bis[4-(4-amino-2-trifluoromethylphenoxy)phenyl]-hexafluoropropane was dissolved in 50 ml of acetone. Then 1.8 g (18.3 mmol) of maleic anhydride was added to the solution, and stirring was continued for 2 hr at room temperature to carry out the reaction between the aromatic diamine and the acid anhydride.

After the reaction the mixture in the form of slurry was filtered, and the separated solid matter was washed with water and dried to obtain 5.1 g of a yellow crystalline product. By chemical analysis, infrared absorption spectrum analysis and NMR analysis the product was confirmed to be 2,2-bis[4-(4-maleamic acid-2-trifluoromethylphenoxy)phenyl]hexafluoropropane. The melting point of this product was 210°-213° C. The yield was 80.6%. FIG. 1 shows the infrared absorption spectrum pattern of the product.

$^{19}$F-NMR (DMSO-d6), standard: CFCl$_3$; $\delta$: $-60.23$ ppm (s, 6F, -CF$_3$); $\delta$: $-63.08$ ppm (s, 6F, F$_3$C+CF$_3$).

EXAMPLE 2

A 100-ml four-necked flask, which was provided with thermometer, stirrer and cooling pipe, was charged with 5.0 g (5.8 mmol) of the bismaleamic acid prepared in Example 1, 20 g of acetic anhydride and 1.5 g of potassium acetate, and stirring was continued for 5 hr at room temperature to carry out the dehydrating and cyclizing reaction of the bismaleamic acid.

After the reaction the mixture in the form of slurry was poured into water, and the solid matter was recovered by filtration, washed with water and dried to obtain 4.6 g of a yellow crystalline substance. By analysis this product was confirmed to be 2,2-bis[4-(4-maleimide-2-trifluoromethylphenoxy)phenyl]hexafluoropropane of 95.8% purity (HPLC analysis). The melting point of this product was 113°–115° C. The yield was 93.3%.

The obtained bismaleimide was refined by recrysallization using ethyl acetate/methanol. The yield of the refined product was about 64%. The refined bismaleimide, which was in the form of yellow crystals, had purity of 99.0% and melting point of 114°–115° C.

$^{19}$F-NMR (DMSO-d6), standard CFCl$_3$; δ: −60.18 ppm (s, 6F, −CF$_3$); δ: −62.88 ppm (s, 6F, F$_3$C+CF$_3$).

EXAMPLE 3

In a 100-ml four-necked flask provided with thermometer, stirrer and cooling pipe, 5.0 g (7.6 mmol) of 2,2-bis[4-(4-amino-2-trifluoromethylphenoxy)phenyl]-hexafluoropropane was dissolved in 50 ml of acetone. Then 1.8 g (18.3 mmol) of maleic anhydride was added to the solution, and stirring was continued for 2 hr at room temperature to carry out reaction between the aromatic diamine and the acid anhydride.

Figure 2:
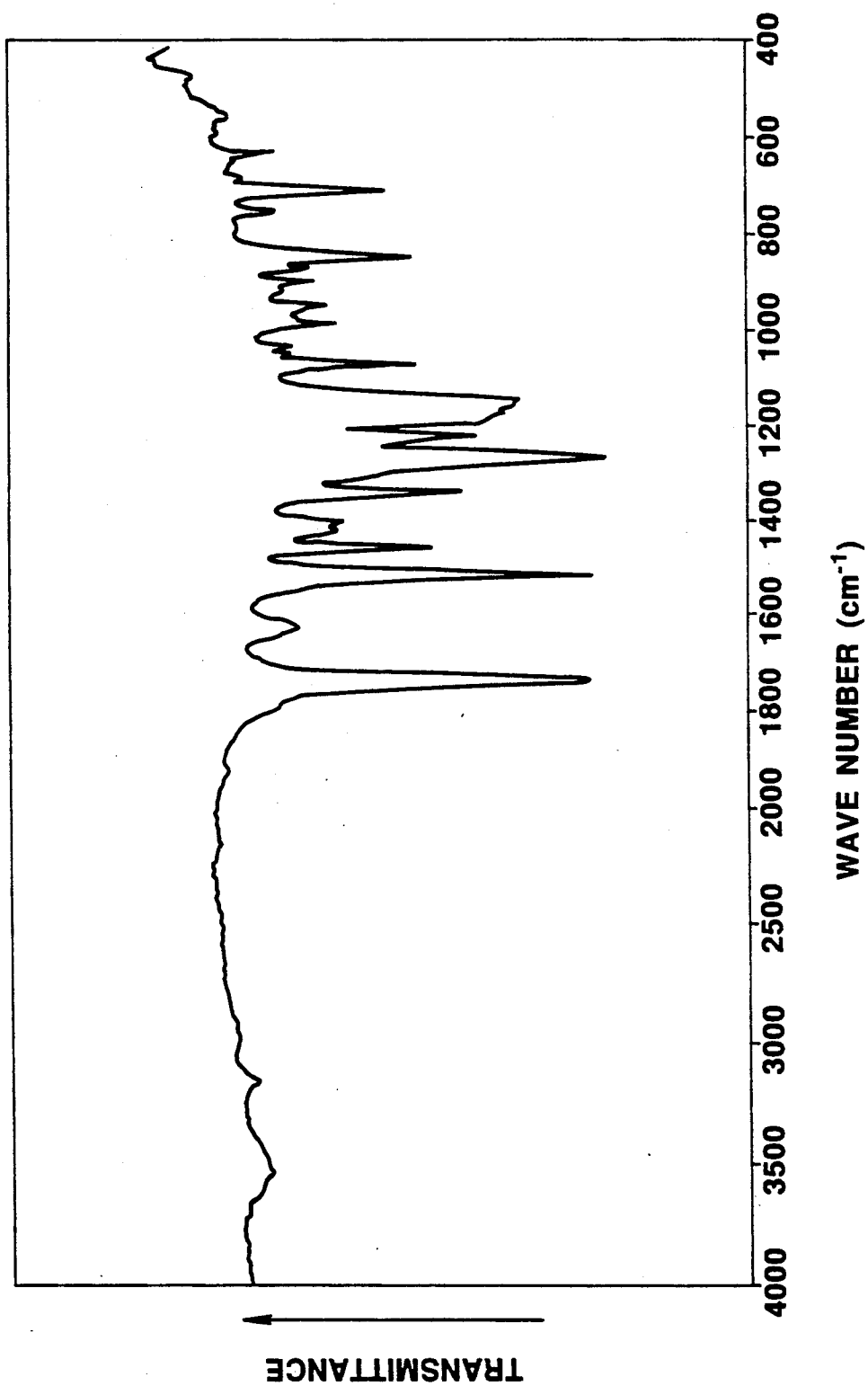
FIG. 2 shows the infrared absorption spectrum pattern of a bismaleimide prepared as an example of the invention.

After that 8 g of acetic anhydride and 1.8 g of triethylamine were added to the mixture in the flask, and stirring was continued for 7 hr at room temperature. Then the slurry in the flask was poured into water, and the solid matter was collected by filtration, washed with water, dried and then refined by column chromatography (silica gel-dichloromethane/n-hexane). As the result 2.3 g of a yellow crystalline substance was obtained. By analysis this product was confirmed to be 2,2-bis[4-(4-maleimide-2-trifluoromethylphenyl)phenyl]-hexafluoropropane of 99.0% purity (HPLC analysis) having a melting point of 114°–115° C. The yield of the refined bismaleimide was 50%. FIG. 2 shows the infrared absorption spectrum pattern of this bismaleimide.

$^{19}$F-NMR (DMSO-d6), standard: CFCl$_3$; δ: −60.18 ppm (s, 6F, -CF$_3$); δ: −62.88 ppm (s, 6F, F$_3$C+CF$_3$).

EXAMPLE 4

A resin composition was prepared by mixing, in a beaker, 10.0 g (12.2 mmol) of 2,2-bis[4-(4-maleimide-2-trifluoromethyphenoxy)phenyl]hexafluoropropane prepared by the same method as in Example 3 with 1.6 g (8.2 mmol) of 4,4'-diaminodiphenylmethane. The molar ratio of the bismaleimide to the diamine was about 1.5:1.

The resin composition was heated to the extent of melting and poured into a shallow glass vessel. Then the resin composition was cured by stepwise heating: first at 180° C. for 1 hr, then at 210° C. for 1 hr, next at 230° C. for 1 hr and finally at 250° C. for 10 hr. As the result a resin plate having a brown color was obtained. The following table shows the glass transition temperature (T$_g$), coefficient of linear expansion, moisture absorption, dielectric constant and dielectric loss tangent of the cured resin.

EXAMPLES 5–8

In these examples the mixing and heat curing operations in Example 4 were repeated except that a different diamine was used in each example: viz. p-phenylenediamine in Example 5, 2,2-bis(4-aminophenyl)-hexafluoropropane in Example 6, 2,2-bis[4-(4-amino-phenoxy)phenyl]hexafluoropropane in Example 7, and 2,2-bis[4-(4-amino-2-trifluoromethylphenoxy)phenyl]hexafluoropropane in Example 8. In every case the molar ratio of the bismaleimide to the diamine was about 1.5:1. In every example the above described stepwise heating of the resin composition resin composition gave a fully cured solid resin plate. The characteristics of the resins of Examples 5–8 were as shown in the table.

|  | Ex. 4 | Ex. 5 | Ex. 6 | Ex. 7 | Ex. 8 |
|---|---|---|---|---|---|
| Glass Transition Temperature (°C.) | 241 | 279 | 250 | 226 | 241 |
| Coefficient of Linear Expansion (25° C. T$_g$: 1/°C.) | 5.78 × 10$^{-5}$ | 6.65 × 10$^{-5}$ | 6.57 × 10$^{-5}$ | 5.76 × 10$^{-5}$ | 5.76 × 10$^{-5}$ |
| Moisture Absorption (D-2/100 (%)) | 0.50 | 0.60 | 0.77 | 0.50 | 0.50 |
| Dielectric Constant (1 MHz, 25° C.) | 3.02 | 3.10 | 2.75 | 2.79 | 2.73 |
| Dielectric Loss Tangent (1 MHz, 25° C.) | 4.45 × 10$^{-3}$ | 5.00 × 10$^{-3}$ | 8.45 × 10$^{-3}$ | 5.74 × 10$^{-3}$ | 9.00 × 10$^{-3}$ |

What is claimed is:

1. A fluorine-containing bismaleimide represented by the formula:

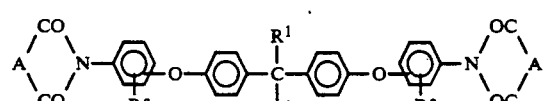

wherein A represents a divalent organic group having an ethylenic unsaturated bond; Rf represents a perfluoroalkyl group wherein, the alkyl contains 1 to 8 carbon atoms; R$^1$ and R$^2$ are the same or different and each represent hydrogen atom, methyl group, ethyl group or a halogenated methyl group; and each —N< is at the m- or p-position with respect to the aromatic ether bond —O—.

2. A bismaleimide according to claim 1, wherein both $R^1$ and $R^2$ in the formula are trifluoromethyl groups.

3. A bismaleimide according to claim 1, wherein both $R^1$ and $R^2$ in the formula are methyl groups, and Rf in the formula is trifluoromethyl group.

4. The bismaleimide of claim 1, wherein A in the formula is

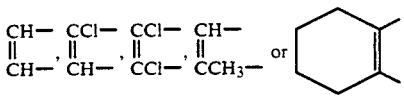

5. A bismaleimide according to claim 2, wherein Rf in the formula is trifluoromethyl group.

6. A bismaleimide according to claim 4, wherein Rf in the formula is trifluoromethyl group.

* * * * *